US006775352B2

(12) United States Patent
Toth et al.

(10) Patent No.: US 6,775,352 B2
(45) Date of Patent: Aug. 10, 2004

(54) METHOD AND SYSTEM FOR IMPLEMENTING VARIABLE X-RAY INTENSITY MODULATION SCHEMES FOR IMAGING SYSTEMS

(75) Inventors: Thomas Louis Toth, Brookfield, WI (US); Bruce Matthew Dunham, Mequon, WI (US); Kelly Lynn Karau, New Berlin, WI (US); Jianying Li, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 160 days.

(21) Appl. No.: 10/064,784

(22) Filed: Aug. 16, 2002

(65) Prior Publication Data

US 2004/0032928 A1 Feb. 19, 2004

(51) Int. Cl.$^7$ ................................. H05G 1/44
(52) U.S. Cl. ................. 378/108; 378/16; 378/101; 378/109; 378/207
(58) Field of Search .................. 378/4, 16, 91, 378/101, 108, 109, 110, 111, 112, 113, 145, 207

(56) References Cited

U.S. PATENT DOCUMENTS

| 5,379,333 A | | 1/1995 | Toth ........................... 378/16 |
| 5,450,462 A | | 9/1995 | Toth et al. .................... 378/16 |
| 5,485,494 A | * | 1/1996 | Williams et al. .............. 378/16 |
| 5,625,662 A | * | 4/1997 | Toth et al. .................... 378/16 |
| 5,680,430 A | * | 10/1997 | Khutoryansky et al. ..... 378/109 |
| 5,696,807 A | | 12/1997 | Hsieh .......................... 378/109 |
| 5,867,555 A | | 2/1999 | Popescu et al. ............... 378/16 |
| 6,067,341 A | | 5/2000 | Horiuchi ........................ 378/8 |
| 6,285,741 B1 | * | 9/2001 | Ackelsberg et al. ......... 378/110 |
| 6,404,844 B1 | | 6/2002 | Horiuchi et al. ............... 378/8 |

FOREIGN PATENT DOCUMENTS

JP 2001043993 A 2/2001

* cited by examiner

Primary Examiner—David V. Bruce
Assistant Examiner—Courtney Thomas
(74) Attorney, Agent, or Firm—Cantor Colburn LLP

(57) ABSTRACT

A method, system and medium for modulating the x-ray power of an imaging system so as to maintain a desired image noise in the imaging system is disclosed. In an exemplary embodiment, the method includes obtaining projection data, correcting the projection data responsive to beam hardening errors so as to create corrected projection data, processing the corrected projection data so as to create a plurality of emitter current values responsive to an imaging method and applying the emitter current values to the imaging system responsive to an object to be imaged. In another aspect, a method for determining an optimum emitter tube voltage for an imaging system includes characterizing the imaging system so as to determine a system water-equivalent path length responsive to a relative noise increase. An object water-equivalent path length is then determined and compared with the system water-equivalent path length so as to create a comparison result, allowing for the recommendation of the optimum emitter tube voltage responsive to the comparison result.

59 Claims, 5 Drawing Sheets

METHOD AND SYSTEM FOR IMPLEMENTING VARIABLE X-RAY INTENSITY MODULATION SCHEMES FOR IMAGING SYSTEMS

BACKGROUND OF INVENTION

The present disclosure relates generally to a variable modulation scheme and more particularly to a variable x-ray power modulation scheme and a method for implementing the variable x-ray power modulation scheme.

In at least one known computed tomography (CT) imaging system configuration, an x-ray source projects a fan-shaped beam which is collimated to lie within an X-Y plane of a Cartesian coordinate system, wherein the X-Y plane is generally referred to as an "imaging plane". An array of radiation detectors, wherein each radiation detector includes a detector element, are within the CT system so as to received this fan-shaped beam. An object, such as a patient, is disposed within the imaging plane so as to be subjected to the x-ray beam wherein the x-ray beam passes through the object. As the x-ray beam passes through the object being imaged, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam attenuation at the detector element location. These electrical signals are referred to as x-ray attenuation measurements.

In addition, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object.

One method for reconstructing an image from a set of projection data is referred to as the "filtered back-projection technique". This process converts the attenuation measurements from a scan into discrete integers, ranging from −1024 to +3071, called "CT numbers" or "Hounsfield Units" (HU). These HU's are used to control the brightness of a corresponding pixel on a cathode ray tube or a computer screen display in a manner responsive to the attenuation measurements. For example, an attenuation measurement for air may convert into an integer value of −1000 HU (corresponding to a dark pixel) and an attenuation measurement for very dense bone matter may convert into an integer value of +2000HU or more (corresponding to a bright pixel), whereas an attenuation measurement for water may convert into an integer value of 0HU (corresponding to a gray pixel). This integer conversion, or "scoring" allows a physician or a technician to determine the approximate density of matter based on the intensity of the computer display.

Certain scanning parameters, such as x-ray tube, or emitter, current ("mA"), x-ray tube supply voltage ("kV"), slice thickness, scan time and helical pitch (for helical scans) are known to affect the x-ray power, which in turn affects image quality. In addition, the x-ray tube current typically directly relates to the patient x-ray dose. A higher x-ray tube current may, for example, improve the image quality but increase the dosage received by the patient. However, lower x-ray tube current levels are known to cause severe streaking artifacts in the image. This is typically caused by an insufficient number of photons passing through the patient and is known as x-ray photon starvation.

Although higher x-ray tube current levels result in lower noise images, the higher x-ray tube current levels subject patients to higher doses of x-ray energy. In conventional CT scanning practice, fixed mA protocols are used to scan a range of patients of various sizes and attenuation characteristics. As a result, the scans of smaller patients have less noise therein than the images of the larger patients. However, since a certain level of diagnostic image quality is required for larger patents, the smaller patients may therefore be receiving more doses than needed for acceptable diagnostic results when fixed mA protocols are used.

With regard to X-ray tube voltage, most CT scanners presently in use provide for several tube voltage stations (for example, 80 kV to 140 kV) that allow a technician and/or physician to adjust the x-ray tube voltage. However, voltage selection is mostly responsive to the preference of the physician, and thus typically lacks scientific guidance. For most body and head scans, some physicians tend to use a tube voltage of 120 kV, whereas others use 140 kV for head and pediatric scans where objects are relatively small. While on one hand higher tube voltage provides for better geometric dose efficiency for larger patients, lower tube voltage has been shown to provide for better contrasts for different types of lesions when the object is relatively small and, therefore, may provide for a better contrast to noise ratio (CNR). Unfortunately, these tradeoffs are not well established for medical practice and as such, the emitter tube voltage selection is generally fixed for a certain type of scan regardless of the patient size. Accordingly, it is desirable to be able to reduce the dose received by individual patients and to improve dose efficiency, while still maintaining acceptably small noise levels and good CNR.

SUMMARY OF INVENTION

The above discussed and other drawbacks and deficiencies are overcome or alleviated by a method for modulating the x-ray power of an imaging system so as to maintain a desired image noise in the imaging system. The method includes obtaining projection data and correcting the projection data responsive to beam hardening errors so as to create corrected projection data. In addition, the corrected projection data is processed so as to create a plurality of emitter current values responsive to an imaging method, and the emitter current values are applied to the imaging system responsive to an object to be imaged.

In another aspect, a method for determining an optimum emitter tube voltage for an imaging system includes characterizing the imaging system so as to determine a system water-equivalent path length responsive to a relative noise increase. An object water-equivalent path length is then determined and compared with the system water-equivalent path length so as to create a comparison result, allowing for the recommendation of the optimum emitter tube voltage responsive to the comparison result.

In another aspect, a system for modulating the emitter current of an imaging system so as to maintain a desired image noise in the imaging system includes a gantry having an x-ray source and a radiation detector array. The gantry defines a patient cavity, wherein the x-ray source and the radiation detector array are rotatingly associated with the gantry so as to be separated by the patient cavity. A patient support structure is movingly associated with the gantry so as to allow communication with the patient cavity. A processing device obtains projection data and corrects the projection data responsive to beam hardening errors so as to create corrected projection data. The processing device processes the corrected projection data so as to create a plurality of emitter current values responsive to an imaging method and applies the emitter current values to the imaging system responsive to an object to be imaged.

In still another aspect, a system for determining an optimum emitter tube voltage for an imaging system includes a gantry having an x-ray source and a radiation detector array. The gantry defines a patient cavity, wherein the x-ray source and the radiation detector array are rotatingly associated with the gantry so as to be separated by the patient cavity. A patient support structure is movingly associated with the gantry so as to allow communication with the patient cavity. A processing device characterizes the imaging system so as to determine a system water-equivalent path length responsive to a relative noise increase. The processing device further determines an object water-equivalent path length and compares the object water-equivalent path length with the system water-equivalent path length so as to create a comparison result, and recommends the optimum emitter tube voltage responsive to the comparison result.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

Disclosed herein is a method and system for determining an X-ray tube current (mA) to maintain a desired image noise, as well as for determining an X-ray tube voltage (kVp) for improved dose efficiency. Briefly stated, for both parameters (tube current and voltage), projection data (i.e., scout data) is used to determine patient size and attenuation characteristics. In the case of tube current, a desired image noise is used to determine an appropriate mA, based upon the scout data. In the case of tube voltage, the scout data is used in conjunction with the desired noise and contrast characteristics to determine an appropriate kVp. As a result, smaller patients can receive smaller doses without image quality being sacrificed.

Figure 1:
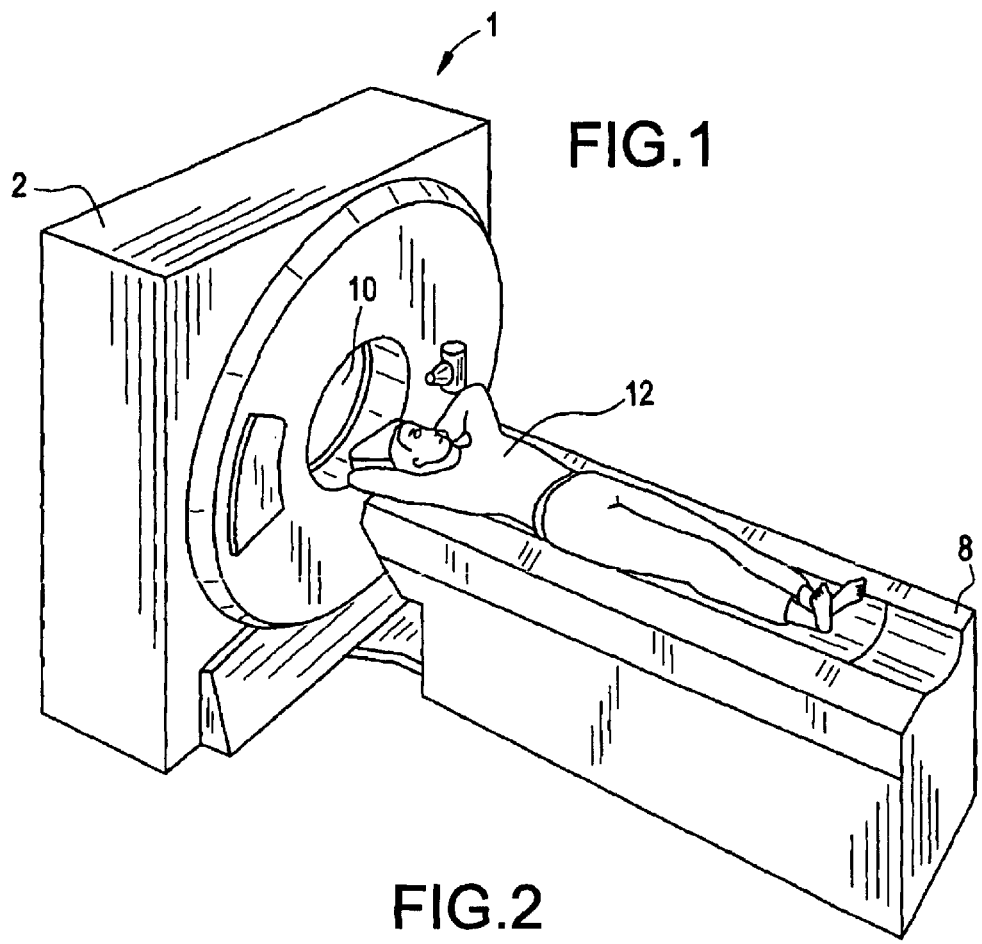
FIG. 1 is a perspective view of a CT imaging system and a patient disposed for imaging.
Figure 2:
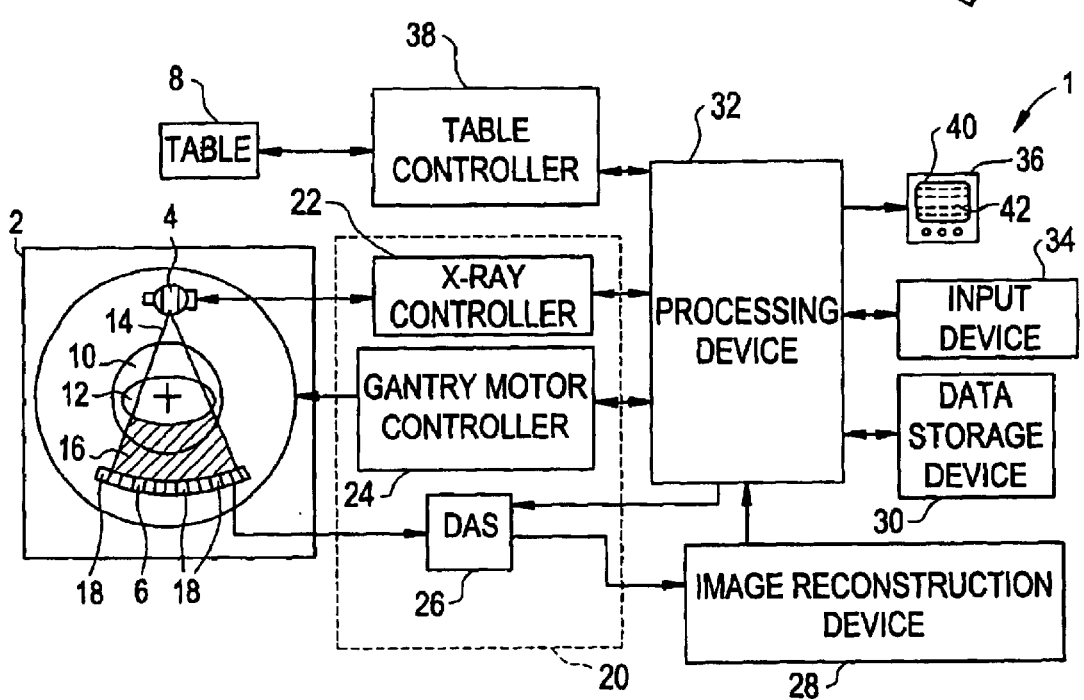
FIG. 2 is a block schematic diagram of a CT imaging system.

Referring initially to FIGS. 1 and 2, there is shown a representative CT imaging system 1 suitable for practicing the present invention embodiments. The system 1 includes a gantry 2 having an x-ray source 4, a radiation detector array 6, a patient support structure 8 and a patient cavity 10, wherein the x-ray source 4 and the radiation detector array 6 are opposingly disposed so as to be separated by the patient cavity 10. A patient 12 is shown disposed upon a patient support structure 8 which in turn is disposed within patient cavity 10. The X-ray source 4 projects an x-ray beam 14 toward radiation detector array 6 so as to pass through patient 12. The X-ray beam 14 is preferably collimated by a collimator (not shown) so as to lie within an X-Y plane of a Cartesian coordinate system referred to as an "imaging plane". After passing through and becoming attenuated by patient 12, the attenuated x-ray beam 16 is received by the radiation detector array 6. The radiation detector array 6 may include a plurality of detector elements 18, wherein each of the detector elements 18 receives an attenuated x-ray beam 16 and produces an electrical signal responsive to the intensity of attenuated x-ray beam 16.

In addition, the x-ray source 4 and radiation detector array 6 are rotatingly disposed relative to the gantry 2 and the patient support structure 8, so as to allow x-ray source 4 and radiation detector array 6 to rotate around the patient support structure 8 when it is disposed within patient cavity 10. X-ray projection data is then obtained by rotating x-ray source 4 and radiation detector array 6 around patient 10 during a scan. The rotation and operation of the X-ray source 4 and radiation detector array 6 are controlled by a control mechanism 20 associated with the CT imaging system 1.

More specifically, the control mechanism 20 includes an x-ray controller 22 in communication with x-ray source 4, a gantry motor controller 24, and a data acquisition system (DAS) 26 in communication with the radiation detector array 6. The x-ray controller 22 provides power and timing signals to x-ray source 4, gantry motor controller 24 controls the rotational speed and angular position of the x-ray source 4, while the radiation detector array 6 and DAS 26 receive the electrical signal data produced by detector elements 18, to be converted into digital signals for subsequent processing. To this end, the CT imaging system 1 also includes an image reconstruction device 28, a data storage device 30 and a processing device 32, wherein the processing device 32 further communicates with the image reconstruction device 28, the gantry motor controller 24, the x-ray controller 22 and the data storage device 30, as well as with an input device 34 and an output device 36. Finally, the CT imaging system 1 also features a table controller 38 in communication with the processing device 32 and the patient support structure 8, so as to control the position of the patient support structure 8 relative to patient cavity 10.

During the operation of the CT imaging system 1, the patient 12 is situated upon then patient support structure 8, which is then positioned by an operator (via processing device 32) within the patient cavity 10. The gantry motor controller 24 is then operated via the processing device 32, thereby causing the x-ray source 4 and the radiation detector array 6 to rotate relative to patient 12. The X-ray controller 22 is operated via processing device 32 so as to cause x-ray source 4 to emit and project a collimated x-ray beam 14 toward radiation detector array 6 and hence toward patient 12. X-ray beam 14 passes through patient 12 so as to create an attenuated x-ray beam 16, which is received by radiation detector array 6.

Upon receiving the attenuated x-ray beam 16, the detector elements 18 produce electrical signal data responsive to the intensity of the attenuated x-ray beam 16, thereafter and communicating this electrical signal data to the DAS 26. The DAS 26 then converts electrical signal data to digital signals and sends both the digital signals and the electrical signal data to the image reconstruction device 28 for high-speed image reconstruction. This image reconstruction information is then communicated to processing device 32, which stores the image in data storage device 30 and displays the digital signal as an image via output device 36.

Figure 3:
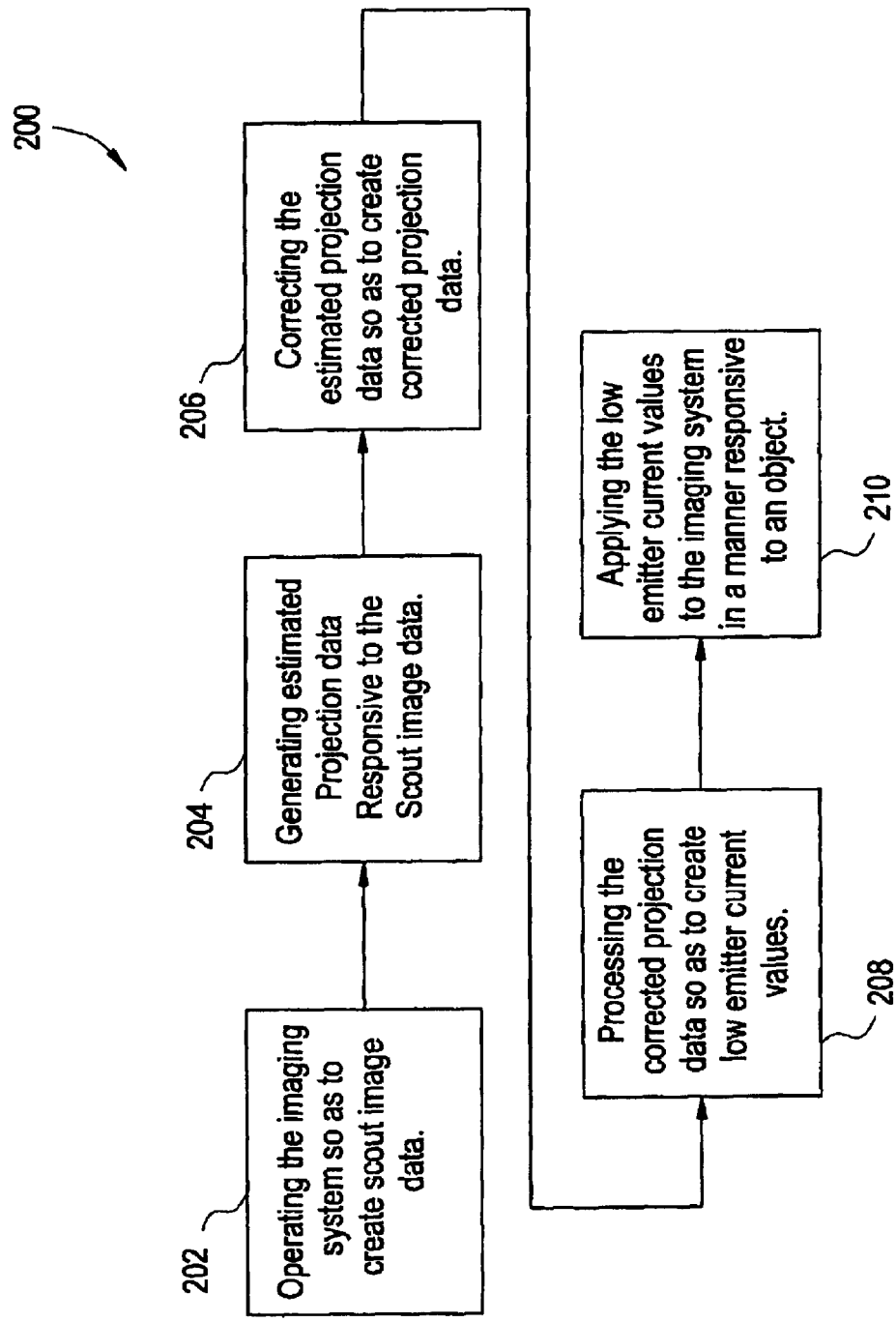
FIG. 3 is a block diagram describing a method for modulating the emitter current of an imaging system.

Referring to FIG. 3, a flow diagram describing a method 200 for modulating the emitter current of an imaging system 1 is shown and discussed. In accordance with an exemplary embodiment, scout image data is created as shown in block 202. Although, scout image data is preferably obtained using CT imaging system 1, scout image data may be obtained using any imaging system suitable to the desired end purpose, such as ultrasound, Positron Emission Tomography (PET), X-Ray and MRI. Moreover, although scout image data is preferably acquired using 120 kV and/or 40 mA, scout image data may be obtained using any emitter voltage (kV) and/or emitter current (mA) suitable to the desired end purpose. The projection data is then generated in a manner responsive to the scout image data as shown in block 204. In order to generate the projection data from scout image data, the scout image data processing steps must be inverted and the scout image data should be clipped or zeroed if it falls below a threshold attenuation value of 0.01. The estimated projection profile for each axial cut through the scout image data may then be generated by inverting the scout image data processing steps using an appropriate equation such as:

$$proj_i = (scout\_image\_row - scout\_shift\_factor)/scout\_scale\_factor * normalization\_factor;$$

wherein scout_image_row is a row of the scout image data and wherein the scout_shift_factor, the scout_scale_factor and the normalization_factor are constants determined a scout reconstruction algorithm.

Similarly, the estimated projection profile, $proj_i$, may be also estimated by applying empirically determined values as shown by the following example equation:

$$proj_i = (image_i - 573)/578.33 * 4.72;$$

wherein the estimated projection profile for each axial cut includes n profile elements (wherein n can have a value of 888, for example) and wherein i is the profile element index. It should be noted that it will be apparent to those skilled in the art that an imaging system may be operated in such a manner so as to produce projection data directly without first producing scout image data which is decomposed into projection data. In addition, although the estimated projection profile for each axial cut is described herein as having 888 profile elements, the estimated projection profile for each axial cut may be composed of any number of elements suitable to the desired end purpose.

Once the projection data has been determined, the projection data is then corrected in a manner responsive to beam hardening errors so as to create corrected projection data, $proj_{gh,i}$, as shown in block 206. This is preferably accomplished applying the following equation:

$$proj_{bh} = a_0 + a_i * proj + a_2 * proj^2 a_3 * proj_i^3 \ldots + a_{bh} * prod_i^k (i=0, n),$$

wherein $a_{0i}, a_{2i}, a_{3i}, \ldots, a_{ki}$ are coefficients responsive to a given kV and imaging filter, and wherein $proj_i$ is the estimated projection profile for a given profile element as discussed hereinabove.

The projection_measure and the projection_area factors are then determined and used to estimate the noise in a given scan using the projection data. The projection_area (PA) is simply the area under the estimated projection profile ($proj_i$) as determined hereinabove, and is given by the following equation:

$$PA = \sum_{i=0}^{887} proj_i$$

wherein i is the profile element. The projection_measure is determined by summing the largest k subset of profile elements as given by the following equation:

$$PM_i = \sum_{i=0}^{99} \{\text{sort}(proj)\}_i$$

wherein the sort is assumed to produce an array in descending order, and wherein j may have a typical value of 100. Moreover, it should be stated that for a round phantom, the projection_measure will be the same no matter what the orientation, but for an elliptical phantom, the projection_measure will vary in a manner responsive to the view and will give a measure of eccentricity in a predetermined scout image plane. In addition, it should be stated that a plot of the projection_area versus the product of the projection measure in two orthogonal planes is given by:

$$PA_i = PM_{0i} * PM_{90,} * S + I.$$

wherein, I is the oval_offset, and S is the oval_Coefficient. As can be seen, this results in a straight line and therefore, if the projection_measure, projection_area and the equation of the line from one scout image plane is known, then the projection measure in the other plane may be predicted.

Using the above factors, the eccentricity, or ovalness, may be determined as follows. Assuming that a 0° projection_measure is known:

$$\text{oval\_ratio} = \frac{PM_{90,i}}{PM_{0,i}} = \frac{(PA_i - I)}{S * PM_{0,i}^2}$$

If the ovalness, Oval_ratio, is less than 1, then it is inverted so that the ratio is always greater than 1. The image standard deviation prediction ($SD_{pred}$), which is an estimate of the image noise for an object that is scanned and reconstructed into an image using a reference set of scan and reconstruction parameters, may then be calculated using the following second order equation:

$$SD_{pred} = a_0 + a_1 X_1 + a_2 X_2 + a_3 X_1 X_2 + a_4 X_1^2 + a_5 X_2^2$$

wherein, $X_1$=(PA*0.001), $X_2$=oval_ratio (if oval_ratio<1, $X_2$=1/oval_ratio) and $a_0$-$a_5$ are predetermined coefficients responsive to a given kV and/or filter. The coefficients are predetermined empirically using well known least squares statistical methods to characterize the noise performance of the imaging system as a function of oval ratio and projection measure. It should be noted that standard statistical practice can sometimes achieve better coefficient fit if the data (noise performance) is transformed by a mathematical operation such as logarithm. For example, if the coefficients are determined for the log10 of the noise data, then the predicted standard deviation is determined by:

$$SD_{pred}=10(a_0+a_1X+a_2X_2+a_3X_1X_2+a_4X_1^2+a_5X_2^2)$$

Once the image standard deviation prediction has been determined for the reference conditions, the emitter current may be calculated so as to produce the image noise desired by the scanner operator ($SD_{desired}$), as shown in block 208. This is preferably accomplished in a manner responsive to an imaging method so as to create a plurality of low emitter current value coefficients, or $autom_A$, that may be used to optimize the emitter current values, or mA, for each type of imaging method, such as axial, helical and/or cine, as given by the following equations:

For axial and cine scan types:

$$mA_{pred} = mA_{ref} * \left(\frac{SD_{pred}}{SD_{desired}}\right)^2 * \left(\frac{scantime_{ref}}{scantime_{actual}}\right) * \left(\frac{slicethickness_{ref}}{slicethickness_{actual}}\right)$$

For helical scan types:

$$mA_{pred} = mA_{ref} * \left(\frac{SD_{pred}}{SD_{desired}}\right)^2 * \left(\frac{scantime_{ref}}{scantime_{acutal}}\right) * helical\_correction\_factor^2$$

wherein, $mA_{ref}$ is equal to 200 mA for baseline noise prediction, $SDP_{desired}$ is equal ref desired to the user requested standard deviation (image noise), $Scantime_{ref}$ is equal to 1 second for baseline noise prediction, $Slicethickness_{ref}$ is equal to 2.5 mm for baseline noise prediction, $Slicethickness_{actual}$ is equal to the user requested slice thickness, $Scantime_{actua}1$ is the user requested scan time and the helical_correction_factor has been determined empirically by finding the noise ratio for all helical techniques relative to a particular helical scan type. The helical_correction_factor compensates for the influence that the helical scan parameters having on the image noise. It is well understood that CT image noise is influenced by patient asymmetry and that the emitter current may be reduced for thinner quadrants without significantly affecting the image noise. Therefore, it is possible to determine the emitter current ($mA_L$) for the thin quadrant from the projection data using the following equation:

$$mA_L = mA_{pred} * \left(\frac{1}{SDR}\right)^2$$

wherein, SDR is the standard deviation ratio which may be determined by computing the $SDR_{pred}$ divided by the $SDR_{pred}$ where the X2 term (oval_ratio) is equated to unity for the denominator calculation.

Figure 4:
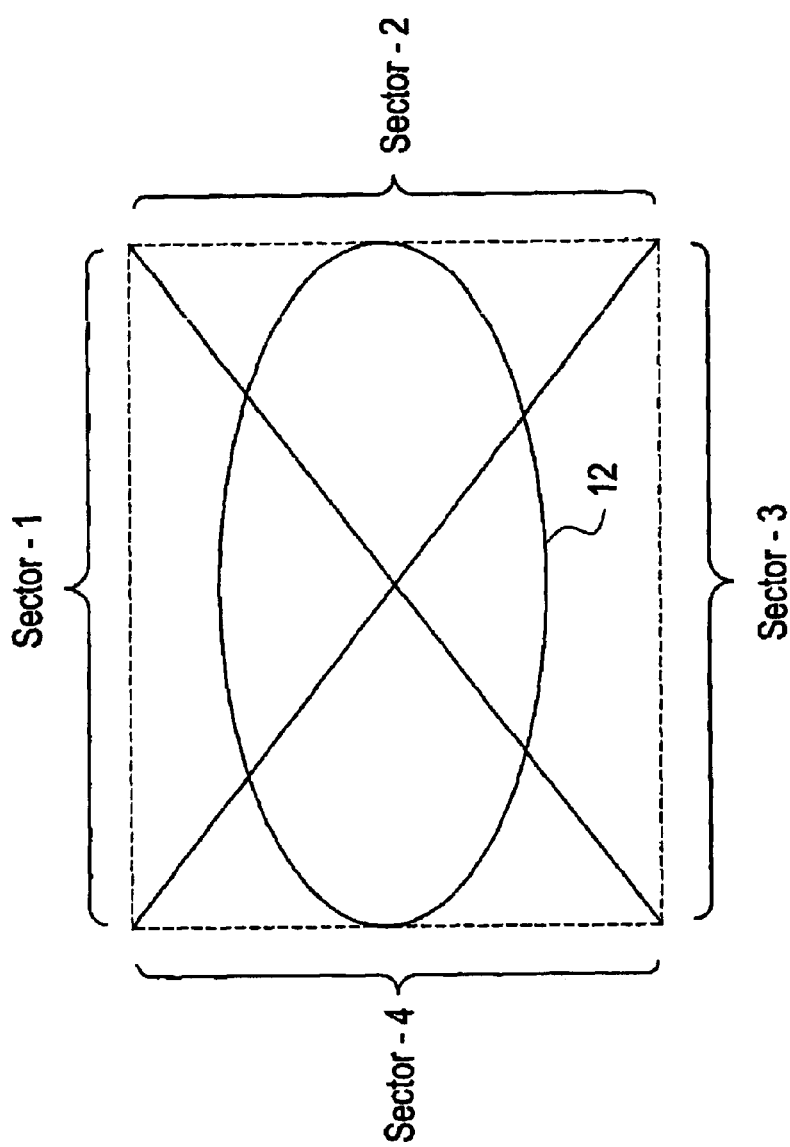
FIG. 4 shows a sector diagram illustrating the thin sectors of an object (Sectors 1 & 3) and the thick sectors of an object (Sectors 2 & 4)

The plurality of predicted emitter current values for the thick sections ($mA_{pred}$) and low emitter current values ($mA_L$) may then be applied to imaging system 1, as shown in block 210. The emitter current values applied during each rotation of gantry 2 are the maximum values over the rotation interval that include the active length of detector array 6 and the movement per rotation of patient support structure 8 which in turn may be dependent upon scan parameters selected by the operator. As such, emitter current, mA, may be applied to imaging system 1 as a function of the angle of gantry 2 and the asymmetry of object 12 without significantly affecting image noise. Therefore, referring to FIG. 4, the amount that the emitter current may be decreased in the thinner quadrants (Sector 1 and Sector 3) is responsive to the oval_ratio for a particular z-location and via simulation, it was determined that the emitter current may be reduced in the thinner quadrants (Sector 1 and Sector 3) as a function of how the standard deviation (image noise) increases. Thus, this relationship is responsive to the oval_ratio. Additional information regarding reducing X-ray exposure on the basis of obtaining a single scout projection set may be found in Japanese Patent JP2001043993, issued to Tetsuya Horiuchi and assigned to GE Yokogawa Medical Systems LTD.

However, it is possible to further reduce dose by considering image noise responsiveness to the oval ratio. A set of curves exists that can be found by fitting image noise data that describe the percentage (%) image noise increase responsive to the % dose reduction for a family of oval ratios at a given kvp and x-ray filtration condition. If it is desired to let the image noise be increased to 5% for example (i.e., a noise increase factor of 1.05), there may be found a coefficient 'c' that describes the dose reduction as a function of oval_ratio by fitting the family of curves at the 5% ordinate:

Rd=(oval_ratio−1)/c

Therefore, substituting this into the equation for the emitter current ($mA_L$) for the thin quadrant as given hereinabove, the lowest achievable emitter current ($mA_L$) value for the thin quadrant that increases the desired image noise by no more than 5% is given by:

$$mA_L = mA_{pred}\left[1 - \left(\frac{oval\_ratio - 1}{\frac{c}{2}}\right)\right]$$

This represents a more aggressive dose reduction (i.e., lower values of $mA_L$ that in the prior art) since the rate of dose reduction exceeds the inverse square root of the noise increase, and hence lower dose for the same image noise is obtained. Values lower than 5% could be used, or both the $mA_{pred}$ and $mA_L$ values could be increased pred L by the inverse square of one minus the noise increase factor if the slight image noise increase is deemed objectionable by some users.

Figure 5:
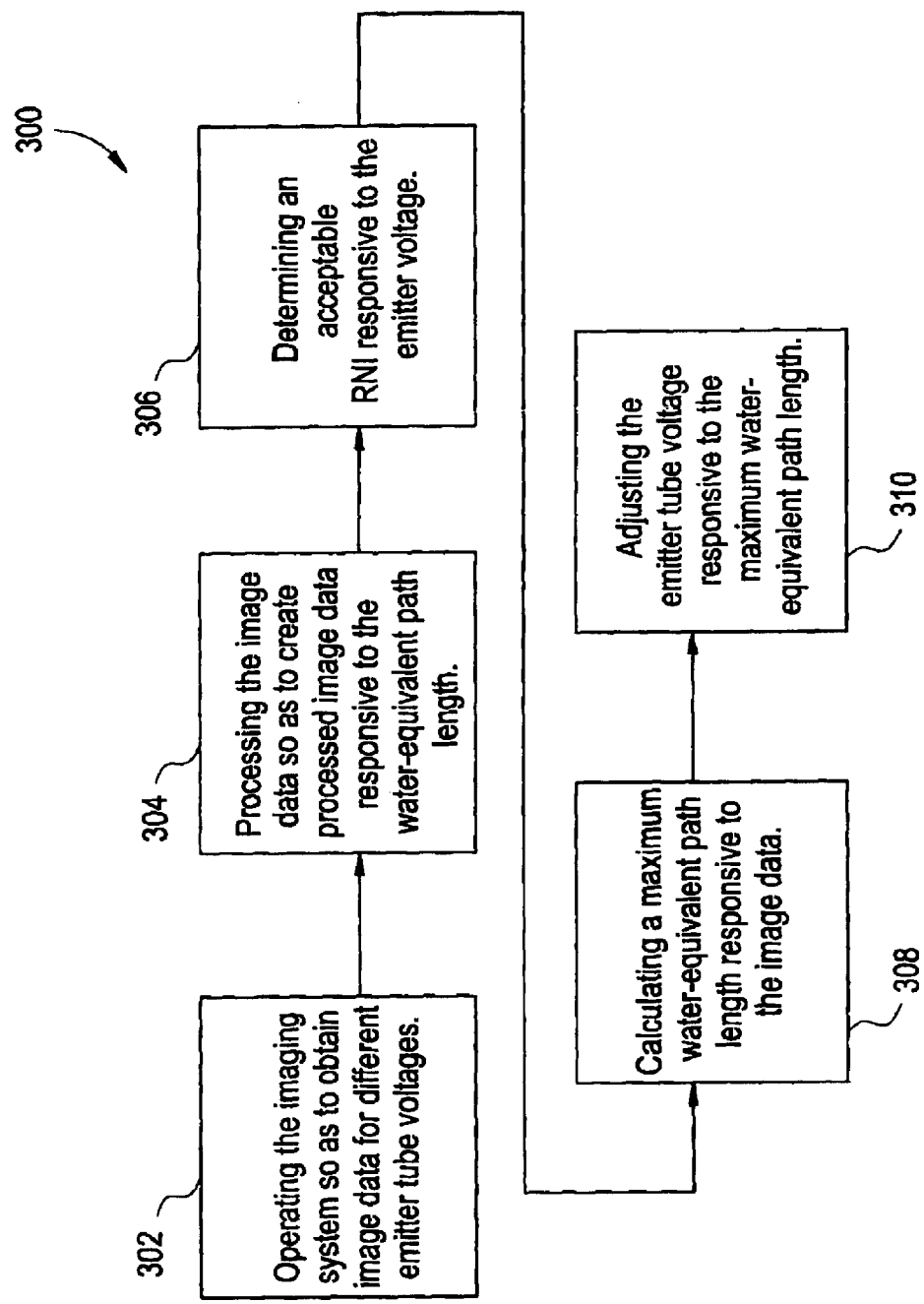
FIG. 5 is a block diagram describing a method for determining an optimum emitter tube voltage for an imaging system.
Figure 6:
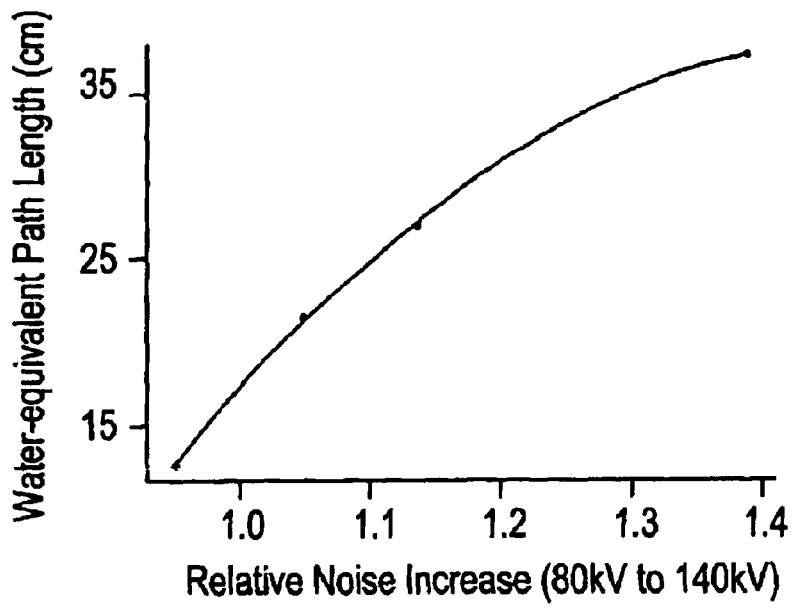
FIG. 6 is a graph of the image noise data for different water-equivalent path length's as a function of the relative noise increase (for the highest system emitter tube voltage) for different emitter tube voltages.

Referring now to FIG. 5, a flow diagram showing a method for determining an optimum emitter tube voltage 300 for an imaging system is shown and discussed. In accordance with an exemplary embodiment, imaging system 1 is operated at a variety of emitter tube voltages (kV) so as to obtain image data responsive to a plurality of emitter tube voltages, as shown in block 302. The emitter tube currents (mA) are then adjusted based on the relative weighted CT Dose Indices (CTDlw) for different emitter tube voltages so as to give an equal CTDlw dose for each emitter tube voltage. Once this has been accomplished, image noise data is obtained for different imaging methods for different water-equivalent path lengths (WEPL) and then normalized to image noise data obtained for the high emitter tube voltage of imaging system 1, in this case 140 kV. The image noise data for the different WEPL's is then plotted as a function of the Relative Noise Increase (RNI) (for the highest emitter tube voltage) for different emitter tube voltages, as shown in FIG. 6. For example, this may be expressed by the following equation:

$$WEPL(80\ kV)=-148.21+247.55*RNI-82.35*RNM2;|$$

wherein RNI is the acceptable relative noise increase of 80 kV relative to 140 kV. If the acceptable relative noise increase of 80 kV relative to 140 kV is equal to or less than 10% (RNI=1.1) for the same CTDlw dose, then the corresponding WEPL needs to be equal to or less then 24.5 cm.

Figure 7:
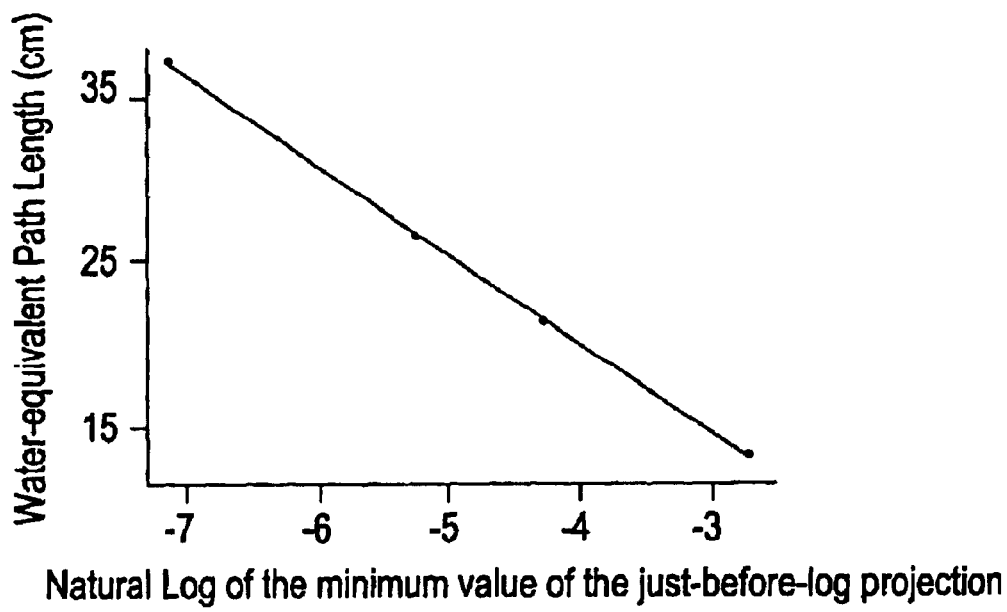
FIG. 7 is a graph of the water-equivalent path length as a function of the natural log of the minimum just-before-log projection and an emitter tube voltage of 120 kV.

Once this has been accomplished, the relationship between the object WEPL and the obtained image data needs to be established. To accomplish this, the obtained image data is processed so as to create processed image data, wherein the processed image data is responsive to different WEPLs, as shown in block 304. The object WEPL responsive to the natural log of the minimum value of the just-before-log projections is then established. This can be seen in FIG. 7, which shows an example plot for the case of 120 kV. This may be accomplished by plotting the curve of WEPL as a function of the natural log of the minimum just-before-log projection (NlogP). For example, one such fit for a 120 kV scan technique may be expressed by the following equation:

$$WEPL = -1.86 - 5.56 * N \log P$$

Based on this equation, if the measured natural log of the minimum value of the just-before-log projection is −4.0, then the WEPL of the object being scanned is approximately 20 cm. Furthermore, the value (−NlogP) is closely related to the PMi stated before. To reduce the impact of a small metal on the determination of the true WEPL of the object, the average of the highest N (100, for example) PMi values may be used here in place of (NlogP) to calculate the WEPL of the object being scanned.

Once this has been accomplished, an acceptable RNI value responsive to the emitter tube voltage (140 kV to 80 kV) is determined, as shown in block 306. This will optimize the Contrast to Noise Ratio (CNR) by allowing imaging system 1 to recommend an alternative imaging method from the default imaging method. Once an acceptable RNI value has been determined, a set of maximum water-equivalent path lengths (MWEPL) below which the emitter tube voltage may be used to increase the CNR is then determined, as shown in block 308. For each scan, imaging system 1 will then use the scout image data to determine the object WEPL of a patient 12, as shown in block 310. The just-before-log projections from the scout image data or the average of the highest N (100, for example) PMi values may then be used to calculate the object WEPL. If the object WEPL is less than the MWEPL that corresponds to the lower emitter tube voltage, then a lower emitter tube voltage may be recommended. On the other hand, if the WEPL is greater than the MWEPL that corresponds to the default emitter tube voltage, then a higher emitter tube voltage may be recommended to increase the geometric dose efficiency.

The method for determining an optimum emitter tube voltage 300 may be used by lowering the emitter tube voltage for patients 12 that have a WEPL smaller than the MWEPL that corresponds to the lower emitter tube voltage. In this case, the emitter tube current may be adjusted based on the CTDlw between the lower emitter tube voltage and the default emitter tube voltage. This advantageously provides a better CNR while maintaining the same imaging dose as the default scan technique. Moreover, the method for determining an optimum emitter tube voltage 300 may also be used by maintaining a CNR equal to the CNR of the default emitter tube voltage while reducing the imaging dose to patient 12. This may advantageously be accomplished by adjusting the emitter tube current to a lower value than the CTDlw determined emitter tube current. Moreover, the method for determining an optimum emitter tube voltage 300 may be used by increasing the emitter tube voltage for patients 12 that have a WEPL greater than the MWEPL that corresponds to the default emitter tube voltage. In this case, the emitter tube current may be adjusted lower based on the CTDlw between the higher emitter tube voltage and the default emitter tube voltage. This advantageously provides images with less noise while maintaining the same imaging dose as the default scan technique. The use of the method for determining an optimum emitter tube voltage 300 may advantageously provide for a better CNR for pediatric or small patient imaging, and lower noise for large adult patient imaging. Moreover, the use of the method for determining an optimum emitter tube voltage 300 may advantageously provide a 15% to 50% imaging dose savings while a constant CNR is maintained.

The disclosed embodiments advantageously allow for objects, such as a patient 12, to be scanned using lower dose scans, thus reducing the energy required to generate larger radiation doses. In addition, potential health problems may advantageously be avoided by reducing the patients' exposure to x-ray radiation to more acceptable levels.

In addition, the processing of FIG. 3 and/or FIG. 5 may be implemented through processing device 32 operating in response to a computer program. In order to perform the prescribed functions and desired processing, as well as the computations therefore (e.g., the execution of Fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include signal input signal filtering to enable accurate sampling and conversion or acquisitions of such signals from communications interfaces. It is also considered within the scope of the invention that the processing of FIG. 3 and/or FIG. 5 may be implemented by a controller located remotely from processing device 32.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for modulating the x-ray power of an imaging system so as to maintain a desired image noise in the imaging system comprising:
   obtaining projection data;
   correcting said projection data responsive to beam hardening errors so as to create corrected projection data;
   processing said corrected projection data so as to create a plurality of emitter current values responsive to an imaging method; and
   applying said emitter current values to the imaging system responsive to an object to be imaged.

2. The method of claim 1, further comprising:
   generating said projection data using an empirical method.

3. The method of claim 1, further comprising:
   operating the imaging system so as to create scout image data; and
   generating said projection data responsive to said scout image data, in accordance with the equation:

$proj_i=(scout\_image\_row-scout\_shift\_factor)/scout\_scale\_factor*normalization\_factor;$ wherein said $proj_i$ is the projection data, said scout_image_row is a row of said scout image data and wherein said scout_scale_factor, said scout_shift_factor and said normalization factor are predetermined constants responsive to a scout reconstruction algorithm.

4. The method of claim 1, further comprising:
   correcting said projection data responsive to beam hardening errors, wherein said projection data includes a plurality of projection data elements, in accordance with the equation:

$proj_{bh,i}=a_0, a_i, *proj_i+a_2*proj_i^2+a_3*proj_i^3, \ldots +a_b*proj_j^k, (i=0, n),$ wherein, said i represents said projection data element, said $a_{0i}$ to said $a_{ki}$ are coefficients responsive to a given emitter tube voltage and an imaging filter and wherein said $proj_i$ is said projection data for said projection data element.

5. The method of claim 1, further comprising generating a projection_measure value, a projection_area value, an eccentricity value and a standard deviation prediction value.

6. The method of claim 1, further comprising:
   generating a projection_measure value, in accordance with the equation:

$$PM_i = \sum_{i=0}^{99} \{sort(proj)\}_i$$

wherein said $proj_i$ is a projection data element and wherein said sort is a mathematical function for producing an array in descending order of the largest j subset of projection data elements.

7. The method of claim 1, further comprising:
   generating a projection_area value, in accordance with the equation:

$$PA = \sum_{i=0}^{887} proj_i$$

wherein, said i is the desired projection element and wherein said $proj_i$ is the $i^{th}$ projection data element.

8. The method of claim 1, further comprising:
   generating an eccentricity value, in accordance with the equation:

$$oval\_ratio = \frac{PM_{90,i}}{PM_{0,i}} = \frac{(PA_i - I)}{S * PM_{0,i}^2}$$

wherein, said $PM_{90,i}$ is the projection_measure for projection data element i at 90 degrees, said $PM_{0,i}$ is the projection_measure for projection data element i at 0 degrees, said $PA_i$ is the projection_area for projection data element i, said I is an Oval_offset coefficient and said S is an oval coefficient.

9. The method of claim 1, further comprising:
   generating a standard deviation prediction value, in accordance with the equation:

$SD_{pred}=a_0+a_1X_1+a_2+a_2X_2X_2+a_4X_1^2+a_5X_2^2$ wherein, said $X_1$=(PA*0.001), said $X_2$=oval_ratio (if oval_ratio<1, $X_2$=1/oval_ratio) and said $a_0$-$a_5$ are predetermined coefficients responsive to a given emitter tube voltage.

10. The method of claim 1, wherein said processing includes determining low emitter current value coefficients, wherein said low emitter current value coefficients optimize said emitter current values.

11. The method of claim 1, wherein said processing includes determining an emitter current value responsive to an axial and cine imaging method, in accordance with the equation:

$$mA_{pred} = mA_{ref} * \left(\frac{SD_{pred}}{SD_{desired}}\right)^2 * \left(\frac{scantime_{ref}}{scantime_{actual}}\right) * \left(\frac{slicethickness_{ref}}{slicethickness_{actual}}\right)$$

wherein, said $mA_{ref}$ is responsive to a baseline noise prediction, said $SD_{desired}$ is responsive to a user requested standard deviation value, said $scantime_{ref}$ is responsive to a baseline noise prediction, said slicethickness$_{ref}$ responsive to said baseline noise prediction, said slicethickness$_{actual}$ is responsive to a user requested slice thickness, said $scantime_{actual}$ is responsive to a user requested scan time and said $SD_{pred}$ is responsive to a predicted standard deviation value.

12. The method of claim 1, wherein said processing includes determining an emitter current value responsive to a helical imaging method, in accordance with the equation:

$$mA_{pred} = mA_{ref} * \left(\frac{SD_{pred}}{SD_{desired}}\right)^2 * \left(\frac{scantime_{ref}}{scantime_{actual}}\right) * helical\_correction\_factor^2$$

wherein, said $mA_{ref}$ is responsive to a baseline noise prediction, said $SD_{desired}$ is responsive to a user requested standard deviation value, said $SD_{pred}$ is responsive to a predicted standard deviation value, said $scantime_{ref}$ is responsive to a baseline noise prediction, said scantime$_{actual}$ is responsive to a user requested scan time and said helical_correction_factor is a predetermined empirical factor responsive to the noise ratio for all helical scan methods relative to a particular helical scan method.

13. The method of claim 10, wherein said low emitter current value coefficients are determined in accordance with the equation:

$$mA_L = mA_{pred}*(1/SDR)^2,$$

wherein, said $mA_{pred}$ is a predicted emitter current for thick portions of said object, and wherein said SDR is a standard deviation ratio responsive to a predicted standard deviation ratio ($SDR_{pred}$).

14. The method of claim 13, wherein said low emitter current value coefficients are determined in accordance with the equation:

$$mA_L = mA_{pred}\left[1 - \left(\frac{\text{oval\_ratio} - 1}{\frac{c}{2}}\right)\right]$$

wherein, c is a coefficient that describes dose reduction as a function of oval ratio such that the desired image noise is increased by no more than about 5%.

15. The method of claim 1, wherein said applying includes applying said low emitter current values in a manner responsive to a gantry angle.

16. The method of claim 1, wherein said imaging system includes a computed tomography imaging system.

17. A medium encoded with a machine-readable computer program code for modulating the emitter current of an imaging system so as to maintain a desired image noise in the imaging system, said medium including instructions for causing a controller to implement a method comprising:

obtaining projection data;

correcting said projection data responsive to beam hardening errors so as to create corrected projection data;

processing said corrected projection data so as to create a plurality of emitter current values responsive to an imaging method; and applying said emitter current values to the imaging system responsive to an object to be imaged.

18. The medium of claim 17, further comprising:

generating said projection data using an empirical method.

19. The medium of claim 17, further comprising:

operating the imaging system so as to create scout image data; and generating said projection data responsive to said scout image data, in accordance with the equation:

$$proj_i = (\text{scout\_image\_row} - \text{scout\_shift\_factor}) / \text{scout\_scale\_factor} * \text{normalization\_factor};$$

wherein said $proj_i$ is the projection data, said scout_image_row is a row of said scout image data and wherein said scout_scale_factor, said scout_shift_factor and said normalization_factor are predetermined constants responsive to a scout reconstruction algorithm.

20. The medium of claim 17, further comprising:

correcting said projection data responsive to beam hardening errors, wherein said projection data includes a plurality of projection data elements, in accordance with the equation:

$$proj_{bh} = a_{0i}a_{1i} + proj_i + a_{2i}*prod_i^1 + a_{3i}*proj_i^3 \ldots + a_{ki}*\text{profit} \ (i=0, n)$$

wherein, said i represents said projection data element, said $a_{0i}$ to said $a_{ki}$ are coefficients responsive to a given emitter tube voltage and an imaging filter and wherein said $proj_i$ is said projection data for said projection data element.

21. The medium of claim 17, further comprising generating a projection_measure value, a projection_area value, an eccentricity value and a standard deviation prediction value.

22. The medium of claim 17, further comprising:

generating a projection_measure value, in accordance with the equation:

$$PM_i = \sum_{i=0}^{99} \{\text{sort}(proj)\}_i$$

wherein said proj is a projection data element and wherein said sort is a mathematical function for producing an array in descending order of the largest j subset of projection data elements.

23. The medium of claim 17, further comprising:

generating a projection_area value, in accordance with the equation:

$$PA = \sum_{i=0}^{887} proj_i$$

wherein, said i is the desired projection element and wherein said $proj_i$ is the $i^{th}$ projection data element.

24. The medium of claim 17, further comprising:

generating an eccentricity value, in accordance with the equation:

$$\text{oval\_ratio} = \frac{PM_{90,i}}{PM_{0,i}} = \frac{(PA_i - I)}{S * PM_{0,i}^2}$$

wherein, said $PM_{90,i}$ is the projection_measure for projection data element i at 90 degrees, said $PM_{0,i}$ is the projection_measure for projection data element i at 0 degrees, said $PA_i$ is the projection_area for projection data element i, said I is an Oval_offset coefficient and said S is an oval coefficient.

25. The medium of claim 17, further comprising:

generating a standard deviation prediction value, in accordance with the equation:

$$SD_{pred} = a_0 + a_1 X_1 + a_2 X_2 + a_3 X_1 X_2 + a_4 X^2 + a_5 X_2^2$$

wherein, said $X_1=(PA*0.001)$, said $X_2$=oval_ratio (if oval_ratio<1, $X_2$=1/oval_ratio) and said $a_0$-$a_5$ are predetermined coefficients responsive to a given emitter tube voltage.

26. The medium of claim 17, wherein said processing includes determining low emitter current value coefficients, wherein said low emitter current value coefficients optimize said emitter current values.

27. The medium of claim 17, wherein said processing includes determining an emitter current value responsive to an axial and cine imaging method, in accordance with the equation:

$$mA_{pred} = mA_{ref} * \left(\frac{SD_{pred}}{SD_{desired}}\right)^2 * \left(\frac{scantime_{ref}}{scantime_{actual}}\right) * \left(\frac{slicethickness_{ref}}{slicethickness_{actual}}\right)$$

wherein, said $mA_{ref}$ is responsive to a baseline noise prediction, said $SD_{desired}$ is responsive to a user requested standard deviation value, said $scantime_{ref}$ is responsive to a baseline noise prediction, said $slicethickness_{actual}$ is is responsive to said baseline noise prediction, said $slicethickness_{actual}$ is responsive to a user requested slice thickness, said $scantime_{actual}$ is responsive to a user requested scan time and said $SD_{pred}$ is responsive to a predicted standard deviation value.

28. The medium of claim 27, wherein said processing includes determining an emitter current value responsive to a helical imaging method, in accordance with the equation:

$$mA_{pred} = mA_{ref} * \left(\frac{SD_{pred}}{SD_{desired}}\right)^2 * \left(\frac{scantime_{ref}}{scantime_{actual}}\right) * helical\_correction\_factor^2$$

wherein, said $mA_{ref}$ is responsive to a baseline noise prediction, said $SD_{desired}$ is responsive to a user requested standard deviation value, said $SD_{pred}$ is responsive to a predicted standard deviation value, said $scantime_{ref}$ is responsive to a baseline noise prediction, said $scantime_{actual}$ is responsive to a user requested scan time and said helical_correction_factor is a predetermined empirical factor responsive to the noise ratio for all helical scan methods relative to a particular helical scan method.

29. The medium of claim 26, wherein said low emitter current value coefficients are determined in accordance with the equation:

$$mA_L = mA_{pred} * (1/SDR)^2;$$

wherein, said $mA_{pred}$ is a predicted emitter current for thick portions of said object, and wherein said SDR is a standard deviation ratio responsive to a predicted standard deviation ratio ($SDR_{pred}$).

30. The medium of claim 29, wherein said low emitter current value coefficients are determined in accordance with the equation:

$$mA_L = mA_{pred}\left[1 - \left(\frac{oval\_ratio - 1}{\frac{c}{2}}\right)\right]$$

wherein, c is a coefficient that describes dose reduction as a function of oval ratio such that the desired image noise is increased by no more than about 5%.

31. The medium of claim 17, wherein said applying includes applying said low emitter current values in a manner responsive to a gantry angle.

32. A method for determining an optimum emitter tube voltage for an imaging system comprising:
characterizing the imaging system so as to determine a system water-equivalent path length responsive to a relative noise increase;
determining an object water-equivalent path length;
comparing said object water-equivalent path length with said system water-equivalent path length so as to create a comparison result; and
recommending the optimum emitter tube voltage responsive to said comparison result.

33. The method of claim 32, wherein said characterizing includes operating the imaging system so as to create pre-scan image projection data responsive to a plurality of emitter tube voltages.

34. The method of claim 33, wherein said object water-equivalent path length is responsive to said pre-scan image projection data.

35. The method of claim 32, wherein said characterizing includes determining said system water-equivalent path length for a plurality of emitter tube voltages, wherein said system water-equivalent path length is responsive to a pre-determined default relative noise increase.

36. The method of claim 32, further comprising:
establishing a relationship between said object water-equivalent path length and said relative noise increase and a maximum allowed emitter tube voltage for the imaging system, wherein said maximum allowed emitter tube voltage is responsive to a known object; and
establishing a relationship between said object water-equivalent path length and the natural log of the minimum just-before-log scan data value, wherein said minimum just-before-log scan data value is responsive to said known object.

37. The method of claim 32, further comprising:
determining said relative noise increase responsive to the emitter tube voltage;
calculating said system maximum water-equivalent path length responsive to said relative noise increase; and
calculating said object water-equivalent path length responsive to a pre-scan image projection.

38. The method of claim 32, further comprising:
adjusting the emitter tube voltage responsive to said comparison result; and
operating the imaging system so as to generate object image data.

39. The method of claim 38, wherein said adjusting includes adjusting emitter tube currents in a manner responsive to a weighted CT Dose Indices at different emitter tube voltages.

40. The method of claim 38, wherein said operating includes normalizing said image noise data in a manner responsive to said emitter tube voltage.

41. The method of claim 32, wherein said relative noise increase is selected so as to optimize the contrast to noise ratio of the imaging system.

42. The method of claim 32, wherein said calculating includes calculating said system water-equivalent path length below which the emitter tube voltage may be used to increase the contrast to noise ratio of the imaging system.

43. A medium encoded with a machine-readable computer program code for determining an optimum emitter tube voltage for an imaging system, said medium including instructions for causing controller to implement a method comprising:
characterizing the imaging system so as to determine a system water-equivalent path length responsive to a relative noise increase;
determining an object water-equivalent path length;
comparing said object water-equivalent path length with said system water-equivalent path length so as to create a comparison result; and
recommending the optimum emitter tube voltage responsive to said comparison result.

44. The medium of claim 43, wherein said characterizing includes operating the imaging system so as to create pre-scan image projection data responsive to a plurality of emitter tube voltages.

45. The medium of claim 44, wherein said object water-equivalent path length is responsive to said pre-scan image projection data.

46. The medium of claim 43, wherein said characterizing includes determining said system water-equivalent path length for a plurality of emitter tube voltages, wherein said system water-equivalent path length is responsive to a pre-determined default relative noise increase.

47. The medium of claim 43, further comprising:
establishing a relationship between said object water-equivalent path length and said relative noise increase and a maximum allowed emitter tube voltage for the imaging system, wherein said maximum allowed emitter tube voltage is responsive to a known object; and
establishing a relationship between said object water-equivalent path length and the natural log of the minimum just-before-log scan data value, wherein said minimum just-before-log scan data value is responsive to said known object.

48. The medium of claim 43, further comprising:
determining said relative noise increase responsive to the emitter tube voltage;
calculating said system maximum water-equivalent path length responsive to said relative noise increase; and
calculating said object water-equivalent path length responsive to a pre-scan image projection.

49. The medium of claim 43, further comprising:
adjusting the emitter tube voltage responsive to said comparison result; and
operating the imaging system so as to generate object image data.

50. The medium of claim 49, wherein said adjusting includes adjusting emitter tube currents in a manner responsive to a weighted CT Dose Indices at different emitter tube voltages.

51. The medium of claim 49, wherein said operating includes normalizing said image noise data in a manner responsive to said emitter tube voltage.

52. The medium of claim 43, wherein said relative noise increase is selected so as to optimize the contrast to noise ratio of the imaging system.

53. The medium of claim 43, wherein said calculating includes calculating said system water-equivalent path length below which the emitter tube voltage may be used to increase the contrast to noise ratio of the imaging system.

54. A method for modulating the emitter current of an imaging system so as to maintain a desired image noise in the imaging system comprising:
obtaining an object to be scanned;
operating the imaging system so as to create image data;
displaying said image data on an output device; and
processing said image data using a processing device, wherein said processing device:
obtains projection data;
corrects said projection data responsive to beam hardening errors so as to create corrected projection data;
processes said corrected projection data so as to create a plurality of emitter current values responsive to an imaging method; and
applies said emitter current values to the imaging system responsive to an object to be imaged.

55. A method for determining an optimum emitter tube voltage for an imaging system comprising:
obtaining an object to be scanned;
operating the imaging system so as to create image data;
displaying said image data on an output device; and
processing said image data using a processing device, wherein said processing device:
characterizes the imaging system so as to determine a system water-equivalent path length responsive to a relative noise increase;
determines an object water-equivalent path length;
compares said object water-equivalent path length with said system water-equivalent path length so as to create a comparison result; and
recommends the optimum emitter tube voltage responsive to said comparison result.

56. A system for modulating the emitter current of an imaging system so as to maintain a desired image noise in the imaging system comprising:
a gantry having an x-ray source and a radiation detector array, wherein said gantry defines a patient cavity and wherein said x-ray source and said radiation detector array are rotatingly associated with said gantry so as to be separated by said patient cavity;
a patient support structure movingly associated with said gantry so as to allow communication with said patient cavity; and
a processing device, wherein said processing device, obtains projection data;
corrects said projection data responsive to beam hardening errors so as to create corrected projection data;
processes said corrected projection data so as to create a plurality of emitter current values responsive to an imaging method; and
applies said emitter current values to the imaging system responsive to an object to be imaged.

57. A system for determining an optimum emitter tube voltage for an imaging system comprising:
a gantry having an x-ray source and a radiation detector array, wherein said gantry defines a patient cavity and wherein said x-ray source and said radiation detector array are rotatingly associated with said gantry so as to be separated by said patient cavity;
a patient support structure movingly associated with said gantry so as to allow communication with said patient cavity; and
a processing device, wherein said processing device, characterizes the imaging system so as to determine a system water-equivalent path length responsive to a relative noise increase;
determines an object water-equivalent path length;
compares said object water-equivalent path length with said system water-equivalent path length so as to create a comparison result; and
recommends the optimum emitter tube voltage responsive to said comparison result.

58. A system for modulating the emitter current of an imaging system so as to maintain a desired image noise in the imaging system comprising:
an imaging system;
a patient support structure movingly associated with said imaging system so as to allow communication between said imaging system and a patient, wherein said imaging system generates image data responsive to said patient; and a processing device, wherein said processing device, obtains projection data;

corrects said projection data responsive to beam hardening errors so as to create corrected projection data;

processes said corrected projection data so as to create a plurality of emitter current values responsive to an imaging method; and applies said emitter current values to the imaging system responsive to an object to be imaged.

59. A system for determining an optimum emitter tube voltage for an imaging system comprising:

an imaging system;

a patient support structure movingly associated with the imaging system so as to allow communication between the imaging system and a patient, wherein the imaging system generates image data responsive to said patient; and a processing device, wherein said processing device, characterizes the imaging system so as to determine a system water-equivalent path length responsive to a relative noise increase;

determines an object water-equivalent path length;

compares said object water-equivalent path length with said system water-equivalent path length so as to create a comparison result; and recommends the optimum emitter tube voltage responsive to said comparison result.

* * * * *